United States Patent [19]
Linder

[11] Patent Number: 5,692,506
[45] Date of Patent: Dec. 2, 1997

[54] TRANSNASAL CONDUIT AND METHOD OF USE

[76] Inventor: Gerald S. Linder, P.O. Box 1085, Pacific Palisades, Calif. 90277

[21] Appl. No.: 695,187

[22] Filed: Aug. 1, 1996

[51] Int. Cl.$^6$ .................................................. A61M 25/00
[52] U.S. Cl. ........................ 128/642; 128/662.06; 607/124
[58] Field of Search .................... 128/642, 662.03, 128/662.06, 207.18, 207.14, 200.26, 911, 912, DIG. 26; 607/124; 604/256, 264

[56] References Cited

U.S. PATENT DOCUMENTS

| | | | |
|---|---|---|---|
| 3,161,199 | 12/1964 | Sands | 128/348 |
| 4,284,076 | 8/1981 | Hall | 128/207.18 |
| 4,300,550 | 11/1981 | Gandi et al. | 128/207.18 |
| 4,645,492 | 2/1987 | Weeks | 604/174 |
| 4,655,214 | 4/1987 | Linder | 128/207.18 |
| 4,671,295 | 6/1987 | Abrams et al. | 128/662.06 |
| 4,722,347 | 2/1988 | Abrams et al. | 128/663 |
| 4,795,442 | 1/1989 | Traflet | 604/179 |
| 4,819,619 | 4/1989 | Augustine et al. | 128/207.18 |
| 4,821,715 | 4/1989 | Downing | 128/207.18 |
| 4,860,757 | 8/1989 | Lynch et al. | 128/657 |
| 4,886,059 | 12/1989 | Weber | 128/662.06 |
| 4,932,943 | 6/1990 | Nowak | 604/180 |
| 5,205,292 | 4/1993 | Czar et al. | 128/662.03 |
| 5,249,580 | 10/1993 | Griffith | 128/662.06 |
| 5,318,017 | 6/1994 | Ellison | 128/200.24 |
| 5,345,940 | 9/1994 | Seward et al. | 128/662.06 |
| 5,370,679 | 12/1994 | Atlee, III | 607/124 |
| 5,388,584 | 2/1995 | King | 128/662.06 |
| 5,484,425 | 1/1996 | Fischell et al. | 604/282 |

*Primary Examiner*—Jennifer Bahr
*Assistant Examiner*—David Ruddy
*Attorney, Agent, or Firm*—Cislo & Thomas LLP

[57] ABSTRACT

A transnasal conduit for transesophageal echocardiography (TEE) probe insertion. A transnasal conduit has a relatively large inner diameter with relatively thin pliable walls. A normally closed or closeable distal end facilitates insertion of the transnasal conduit into the patient during intubation. Pinch clamp means in the form of a thumbscrew or the like may be used to secure a probe temporarily to the transnasal conduit both during and after intubation. A patient flange having ears or lobes may be adjacent the pinch clamp and serve to temporarily secure the transnasal conduit along with any accompanying probe to the patient by means of an elastic strap, string, or the like. The open proximal end of the transnasal conduit may be bell shaped, or flared, to facilitate introduction of the probe. By providing a transnasal conduit that allows atraumatic of a TEE probe, conscious ICU or ambulatory patients may be monitored using TEE thereby enhancing patient diagnosis and monitoring.

10 Claims, 1 Drawing Sheet

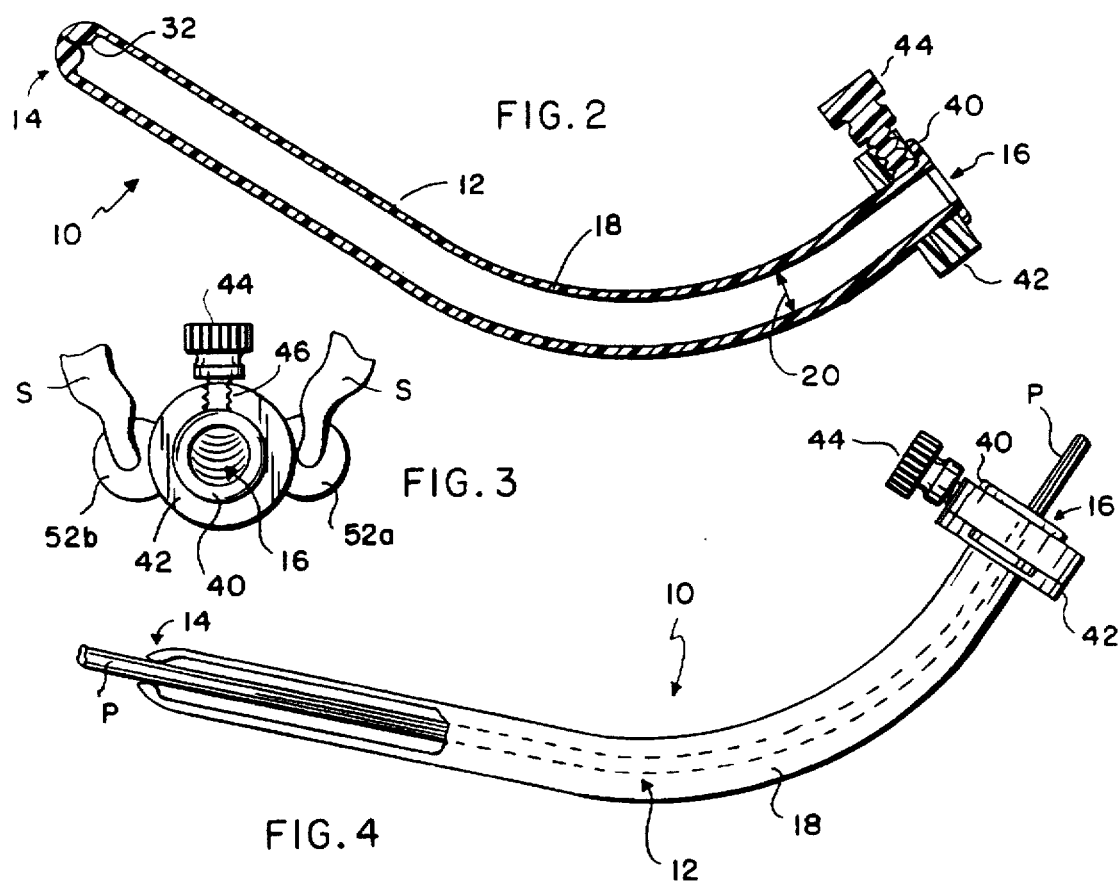

TRANSNASAL CONDUIT AND METHOD OF USE

BACKGROUND OF THE INVENTION

1. Field of the Invention

The present invention relates generally to nasopharyngeal airways (NPAs) and more particularly to a nasal conduit allowing the atraumatic introduction of probes and diagnostic instruments, particularly transesophageal echocardiography (TEE) sensors.

2. Description of the Related Art

Transesophageal echocardiography (TEE) allows physicians to diagnose myocardial function and ischemia during surgery. With TEE surgeons can concurrently assess surgical repairs made during surgical procedures as TEE provides contemporaneous indication of the patient's cardiac and circulatory condition. With TEE, higher initial surgical success rates accompanied by a reduction of complications has been achieved.

In order to position TEE probes, insertion is often made through the mouth. While this procedure is generally safe, manipulation of the TEE probe can produce dental, pharyngeal, laryngeal, and esophageal injuries. Additionally, orally inserted TEE probes are not well tolerated by conscious patients as the probes tend to move with the patient. With the decreased tolerance by conscious and even ambulatory patients, TEE probes have limited use for dynamic tests such as stress treadmill and exercise echo cardiogram tests and the like. However, there is a great interest in achieving use of a TEE probe in ambulatory patients as TEE allows direct diagnosis of a multitude of cardiac abnormalities.

TEE provides more comprehensive information regarding cardiac performance than electrocardiography (ECG) and pulmonary artery catheters (PAC). Images generated through TEE are also better than transthoracic echocardiography (TTE), which cannot be used when the chest is open. Certain medical advantages arise with TEE in that TEE is not blocked by operating-room monitors, drapes, and/or surgical equipment. However, epicardial echocardiography (EE) probes require a sterile field and can interfere with surgery, they are also removed when the chest is closed therefore terminating any useful monitoring of the patient. TEE, on the other hand, provides continuous monitoring as well as important patient condition information such as abnormalities in myocardial wall motion and perivalvular leakage without requiring an invasive surgical procedure.

TEE currently provides means by which a patient's condition can be monitored closely without requiring surgery. However, orally inserted TEE probes are generally used for only relatively short time intervals and mostly in unconscious patients due to the difficulties indicated above. For intensive-care unit (ICU) patients who are conscious, it is highly desirable to have a long-term TEE monitoring the patient continually so that such patients may be diagnosed rapidly and treated appropriately. Additionally, use of TEE probes in conscious patients could be accomplished, thereby allowing dynamic TEE monitoring, if a TEE probe could be placed within a patient via a nasal instead of an oral route.

Transnasal insertion of a relatively large-bore TEE probe or the like can inflict trauma upon the nasal mucosa due to the requirements of the TEE probe's electrical signal surface. That surface must generally be wedge-shaped. It is possible to transnasally insert TEE probes through previously inserted nasopharyngeal airways (NPAs).

The object in using NPAs for probe placement is to avoid bleeding and trauma to the nose during insertion and subsequent probe manipulation. Conventional NPAs, however, are limited as to their usefulness as they may damage the nasal mucosa and nasal structure because of their open, beveled tip. Additionally, NPAs are commonly relatively thick walled, thereby limiting the useful inner diameter for passage of the TEE probe. The relatively small inner diameter of NPAs may deny TEE probe access to a significant segment of the smaller sized adult population which experiences heart and circulatory difficulties to the same degree as other segments of the adult population.

Use of NPAs with large inner diameters may still pose difficulties when used in conjunction with TEE probes. While such NPAs may be atraumatically inserted into the patient, it remains often difficult to pass TEE probes through them. Additionally, patients can forcefully expel the NPA from their naris occasionally.

As can be seen, it would be an advancement in the art to provide a transnasal conduit or the like that would allow atraumatic intubation of a TEE probe. Furthermore, such a transnasal conduit should not only resolve the foregoing problems but should also prevent its own migration into the naris as NPAs with small or ill-defined flanges can so migrate. Additionally, such a transnasal conduit should advantageously maintain the probe position relative to the conduit by allowing controlled, temporary securement of the probe to the transnasal conduit.

With the realization of a transnasal conduit allowing the nasal insertion of a TEE probe, conscious ICU, ambulatory, and other patients for whom TEE probes are generally unavailable at the present could now be intubated with a TEE probe transnasally in order to closely monitor contemporaneous cardiac and circulatory function. Better patient diagnosis and earlier detection of cardiac and circulatory symptoms, problems, or anomalies for increased patient care and more efficient allocation of health-care resources could then be provided.

Currently, no such transnasal conduits are known in the art that resolve the disadvantages of using current NPAs while addressing the shortcomings of current TEE probe insertion procedure.

SUMMARY OF THE INVENTION

The transnasal conduit of the present invention provides a thin walled, large inner diameter conduit for the insertion of a TEE probe into the patient. Such intubation of the TEE probe occurs transnasally, thereby allowing ambulatory use of the TEE probe in conjunction with conscious patients. Current patient cardiac and circulatory status are thereby better monitored and the patient may be subjected to stress (as with a treadmill or other stress test) while the TEE probe is present. Additionally, ICU patients may be continuously monitored via TEE without suffering the disadvantages with orally inserted TEE probes.

The transnasal conduit of the present invention has a relatively large inner diameter and relatively thin walls. The relatively large inner diameter provides room for large-bore TEE probes. The thin walls are pliable but protect delicate mucosal tissues adjacent to the walls after intubation.

The distal end of the transnasal conduit is normally closed or closeable so that a smooth, generally atraumatic conduit surface is initially brought into contact with any surrounding tissue as the transnasal conduit is intubated into the patient. The proximal end of the transnasal conduit is generally flared or has an extended flange shape and is continuous and coterminous with this proximal end to allow the easy introduction of the TEE probe or the like. A pinch clamp means or a collar or the like may be used adjacent the flared end and may have a thumbscrew supported therein for releasably attaching a TEE probe or the like to the transnasal conduit. The screw clamp collar is captively retained between the proximal flared or flanged end and the more distal, larger, eared patient flange (as described below).

In order to prevent further migration of the transnasal conduit into the patient, a second and more distal flange may be used in conjunction with the collar that allows releasable attachment of the transnasal conduit to the patient's head. The flange may be "eared" as in having lobes with holes or the like through them. An elastic strap, string, or the like may pass through the lobes to provide temporary attachment. Additionally, adhesive means may be used to temporarily attach the transnasal conduit to the patient.

In use, a well lubricated TEE probe is initially inserted into the conduit until the tip of the probe is within the closed dome or adjacent to the distal conduit tip. Under such circumstances the entire interior lumen of the transnasal conduit is generally accompanied by the presence of at least a portion of the TEE probe. The thumbscrew, pinch clamp means, or other clamping means is tightened to temporarily hold and maintain the TEE probe in relative position with the transnasal conduit. The conduit is then externally lubricated and the conduit-probe assembly is configured by a probe directional mechanism into an NPA curve shape to curvedly conform to the anticipated internal geometry of the patient's transnasal passage.

The conduit and probe forming the assembly are simultaneously inserted and passed through the naris and into the oropharynx. During this procedure, the enclosed probe acts as the introducer to support the sheathing transnasal conduit. Upon full insertion of the transnasal conduit with its probe into the patient, the pinch clamp is released, freeing the probe from its attachment to the transnasal conduit. The probe is advanced through the segmented dome or round distal conduit tip to expose the distal end of the probe. The probe is inserted into the esophagus where patient monitoring may occur. The pinch clamp is then re-tightened by turning the thumbscrew to reengage the TEE probe, thereby re-attaching it to the transnasal conduit to hold the TEE probe in place. Removable attachment of the transnasal conduit to the patient is achieved by the patient-contacting eared flange with its elastic strap.

Alternative embodiments include alternative distal tip configurations. Such alternate distal tip configurations may include a closed diaphragm which opens when a probe is pushed through it as well as a membranous balloon shaped tip which ruptures cleanly when the probe is passed through it. Both of these alternate distal tip configurations allow generally atraumatic insertion of the transnasal conduit with the accompanying probe due to the soft, rounded end of the distal tip configuration.

OBJECTS OF THE INVENTION

It is an object of the present invention to provide a transnasal conduit for TEE probes and the like.

It is another object of the invention to provide a transnasal conduit for TEE probes that generally provides atraumatic insertion of the TEE probe.

It is an additional object of the present invention to provide a transnasal conduit with a closed or normally closable end so that the transnasal conduit may be atraumatically introduced into the patient.

It is yet another object of the present invention to provide a transnasal conduit which does not migrate with respect to the patient.

It is another object of the present invention to provide a transnasal conduit that provides easy TEE probe passage.

It is yet another object of the present invention to provide a transnasal conduit that is releasably attachable to the associated TEE probe.

It is yet another object of the present invention to provide a transnasal conduit that is releasably attachable to the patient.

These and other objects and advantages of the present invention will be apparent from a review of the following specification and accompanying drawings.

BRIEF DESCRIPTION OF THE DRAWINGS

FIG. 1 is a side perspective view of the transnasal conduit of the present invention.

FIG. 2 is a side cross sectional view of the transnasal conduit of FIG. 1 taken along line 2—2.

FIG. 3 is a plan view of the open proximal end of the transnasal conduit of FIG. 1.

FIG. 4 is a side plan view of the transnasal conduit of FIG. 1 showing in partial cutaway section a TEE probe projecting through the distal tip of the transnasal conduit.

DESCRIPTION OF THE PREFERRED EMBODIMENT(S)

As shown in FIG. 1, the transnasal conduit 10 of the present invention has an elongated tube or catheter 12 with a normally-closed distal end 14 and an open proximal end 16. The tube 12 is made of surgically-acceptable, pliable plastic or the like that is soft and generally bendable. The material used to construct the tube 12 may maintain a curved shape as shown in FIGS. 1, 2, and 4, yet may compliantly bend to conform to any number of configurations (especially such configurations as the transnasal conduit 10 can be expected to attain when inserted into the patient).

The tube 12 may be on the order of 4 to 8 inches long to accommodate the different lengths of nasal passages in adults of different sizes. The tube 12 is generally thinned walled with the thickness of the wall 18 being on the order of a few millimeters (approximately one tenth of an inch). The inner diameter 20 of tube 12 is approximately 7.4 mm to 9.4 min. This inner diameter may be adjusted according to the size and type of patient in order to accommodate their nasal passages.

The distal end 14 of the tube 12 is shown in the figures as having three separate lobes 30. The normally closed, trilobed ball end 14 as is shown in the figures is but one embodiment that may be achieved in the present invention. The individual lobes 30 are generally constructed of the same pliable, surgically approved materials. The distal end 14 of the present invention is generally formed concurrent or contemporaneously with the tube 12. As shown in FIG. 2, each lobe 30 has underlying its outer surface an interior protuberance 32 that conforms with the lobe 30 of the distal tip 14. The protuberances 32 serve to elastically hold closed the lobes 30 so that the distal end 14 may pass more easily and generally atraumatically through the patient during intubation. Each of the individual lobes 30 is separated from the other lobes 30 by separation lines 34 that generally extend only along the distal tip 14. The separating lines 34 arise from the separation of each of the individual lobes 30 and show the abutment of each of the lobes 30 against one another.

The tube 12 may have internal striations providing easier insertion and passage of the probe. Such striations are contemplated as travelling the length of the tube 12 from the open proximal end 16 to the distal end 14.

The open proximal end 16 of the tube 12 may be flared or flanged in shape, much like a bell, so as to provide easier introduction of probes and the like. Thus, as shown in FIGS. 2 and 4, the open proximal end 16 of the conduit 10 is circumscribed by a flange 40 that is continuous and coterminous with the tube 12. The flange 40 provides an abutting surface by which larger structures such as the collar 42 and/or the flange 50 may prevent migration of the transnasal conduit 10 further into the naris of the patient once full insertion of the transnasal conduit has been achieved. By providing an abutting surface against which other structures circumscribing the perimeter of tube 12 may engage and have their further forward travel prevented, the flange 40 provides a safer, more advantageous, and useful transnasal conduit that maintains its position relative to the patient.

As shown in FIGS. 1 through 4, a collar 42 generally circumscribes the tube 12 immediately adjacent the flange 40. The collar 42 may be made of surgically approved plastic materials or the like and may slide about the exterior of tube 12. Generally, the collar is positioned adjacent the flange 40 for easy manipulation and full insertion of the transnasal conduit 10 into the patient. The collar is approximately a centimeter in length so that it may fully engage a thumbscrew 44 or the like via the threaded aperture 46.

Thumbscrew 44 threadingly engages the collar 42 and travels perpendicularly to the adjacent tube wall 18. When the thumbscrew 44 is turned so as to travel towards tube 12, probes or other devices previously inserted into the open proximal end 16 of the transnasal conduit 10 may be pinched, clamped, or otherwise releasably attached to the transnasal conduit 10 by trapping such probes between opposite sides of tube 12. The pliable walls 18 flex so as to trap the probe between thumbscrew 44 and collar 42.

While a thumbscrew threadingly engages the collar 42 is set forth herein, other pinch clamp means may also be advantageously used in conjunction with the present invention to releasably attach probes or the like relative to the transnasal conduit 10.

The thumbscrew 44 may also be constructed of surgically-approved materials including plastic or the like. The thumbscrew 44 is sufficiently held by the collar 42 so that the thumbscrew 44 may press down upon the pliable materials composing the wall 18 of the tube 12. The pliable nature of the wall 18 allows the thumbscrew to press into the tube 12 to compress any adjacent probe or the like. The pliable nature of wall 18 allows the wall 18 to maintain structural integrity which also provides means by which releasable attachment may be made of probes or the like to the transnasal conduit 10.

As shown in FIG. 1, an additional, more distally located flange may circumscribe the exterior of tube 12. "Eared" patient flange 50 serves as patient attachment means by which the transnasal conduit 10 may be removably attached to the patient in order to better secure the transnasal conduit 10 to the patient and providing for greater patient comfort and securement of the device. The patient flange 50 is generally circular in nature with a central aperture through which the tube 12 may slidably pass until the patient flange 50 engages the collar 42. The patient flange 50 is generally shorter in length than the collar 42 as it need not support any thumbscrew or similar device. The patient flange 50 may be generally the same diameter as the collar 42.

On opposing sides and extending laterally outward from the perimeter of the patient flange 50 are two lobes or ears 52a, 52b. These flange lobes are each apertured with a single hole so as to provide an aperture through which a preferably elastic string, strap, or other similar device may be used so that the transnasal conduit 10 may be removably attached to the patient. As shown in FIG. 1, a strap S is used and is generally doubled back so that the strap S may be encircled about the patient's head. This holds the transnasal conduit 10 in position upon the patient. As with the other elements of the present invention, the patient flange 50 may be constructed of surgically approved materials such as plastic or the like. As with the other elements of the present invention, it is best to avoid latex or latex-based materials in order to reduce the risk of any allergic reaction to such latex materials. As contemplated in the present invention, all materials used are not only approved for surgical use, but are preferably hypo-allergenic as well.

Having described the construction of the present invention, its operation is as follows. Reference may be made to FIG. 4 in conjunction with the following description. In order to introduce a transesophageal echocardiography (TEE) probe into a patient for contemporaneous monitoring of cardiac and/or circulatory function or the like, the probe P is initially well lubricated for insertion into the transnasal conduit 10. Such lubrication mainly serves to facilitate the passage of the probe P into the transnasal conduit 10. However, it also serves as means by which injury may be avoided to the patient once the distal end of the probe P emerges from the distal end 14 of the transnasal conduit 10.

Upon insertion of the lubricated probe P into the transnasal conduit 10, the distal end of the probe P is inserted into the tube 12 until the distal probe P is generally adjacent, but well within the distal end 14 of the transnasal conduit 10. Thumbscrew 44 or other pinch clamp means is then tightened to secure the probe P relative to the transnasal conduit 10. By tightening the thumbscrew 44, the end of the thumbscrew 44 engages the wall 18 of tube 12. Thumbscrew 44 compresses the wall 18 until it comes into contact with the probe P. The probe P is then secured between the wall 18 adjacent thumbscrew 44 and the wall 18 on the opposite side which is held in place by the portion of collar 42 opposite the thumbscrew 44. The wall 18 is held in place between the collar 42 and the thumbscrew 44. Upon so securing the probe P relative to the transnasal conduit 10, the probe P is then bent into a configuration that allows easier passage while the conduit-probe assembly is slowly inserted into the patient. The disposition of the probe P and the conduit 10 may be such as to anticipate the anatomy of the patient and may achieve its initial configuration with the use of a probe directional mechanism (not shown).

Once the proper configuration is achieved by the conduit-probe assembly, the exterior of the tube 12, particularly distal end 14, is well lubricated. Intubation of the conduit-probe assembly is initiated by inserting the distal tip end 14 into an open naris of the patient. Intubation then continues until the transnasal conduit 10 is fully inserted into the patient with the patient flange 50 engaging the open naris end and with the patient flange 50 abutting the collar 42 and preferably abutting collar 42 and flange 40. As the probe P is generally stiffer than the soft, pliable tube 12, probe P acts as an introducer for the transnasal conduit 10 during intubation.

Upon full insertion of the transnasal conduit 10 into the patient, the intubation process is not yet complete. The distal end of the TEE probe P has an electrical signal surface which is used to monitor the patient's condition. Generally, this probe is semi-wedge shaped due to the electrical signal surface area requirements.

The distal end of the probe P must be brought into the esophagus in order to properly monitor the patient. In order to do so, it must emerge from the distal end 14 of the transnasal conduit. By unthreading thumbscrew 44 or otherwise loosening the pinch clamp, the probe P may be released from its temporary attachment to the transnasal conduit 10 and further inserted into the patient. In so doing, the probe P continues to pass though the transnasal conduit 10 to emerge from the distal conduit end 14. As probe P was previously lubricated prior to insertion into the transnasal conduit 10, such lubrication serves to facilitate passage of the probe P through the tube 12 and also serves to allow easier insertion of the probe P into the patient's esophagus with minimal trauma.

Once probe P is in place, the thumbscrew 44 or other pinch clamp means are tightened so as to secure the probe P with respect to the transnasal conduit 10. This holds the probe P in position with respect to the patient's esophagus and prevents any relative travel between the transnasal conduit 10 and the probe P. In order to temporarily hold the conduit-probe assembly to the patient, a strap S (FIG. 1) is threaded through the holes 54 in the ears or lobes 52a, 52b of the patient flange 50. In one embodiment, the strap may take the form of an elastic band that is secured to the patient flange 50. The strap S is of such length so as to allow elastic encirclement of the strap S about the patient's head, thereby removably attaching the patient flange 50 and the associated transnasal conduit 10 to the patient.

Upon securing the transnasal conduit 10 with the associated TEE probe P to the patient, conscious ICU or ambulatory patients may now be continuously monitored with TEE for diagnostic and monitoring purposes.

Alternative embodiments of the present invention include alternative distal tip 14 configurations. In one alternative embodiment, a closed diaphragm is used at the closed distal end 14 of the transnasal conduit 10. The closed diaphragm end opens up when the probe P is pushed through it. Additionally, another alternative embodiment exists in use of a membranous balloon-shaped tip which provides and facilitates atraumatic insertion of the conduit-probe assembly into the patient. The membranous, balloon-shaped tip is then ruptured cleanly when the thumbscrew 44 is loosened and the probe P is pushed through the membranous, balloon-shaped tip.

Additionally, a pleated rubber or plastic dome or a thicker unpleated shape may be used at the distal tip 14 of the transnasal conduit 10. Alternatively, a stiffer unpleated domed shaped tip 14 may prove satisfactory.

While the present invention has been described with regards to particular embodiments, it is recognized that additional variations of the present invention may be devised without departing from the inventive concept.

What I claim is:

1. A transnasal conduit for atraumatically guiding a member through delicate mucosal passages of a patient, comprising:

a tube, said tube having a relatively thin and pliable wall and a single relatively wide inner diameter with respect to the mucosal passages;

said tube having an open proximal end for introduction of a member into said tube;

said tube having a plurality of separate lobes formed at a distal end of said tube, said plurality of lobes being contoured to be disposed in abutting relationship for forming a normally closed distal end for promoting atraumatic travel of said tube through the mucosal passages, said plurality of separate lobes being displaceable to open said distal end of said tube responsive to a force applied thereto by advancement of the member through said tube;

a flange, said flange circumscribing said open proximal end of said tube, said flange providing an abutting surface that helps prevent migration of said tube further into a naris associated with the mucosal passages past said open proximal end; and clamping means for depressing said thin and pliable wall of said tube to temporarily and releasably clamp the member to said tube.

2. The transnasal conduit of claim 1, wherein said relatively thin and pliable wall of said tube is approximately one to three millimeters thick.

3. The transnasal conduit of claim 1, wherein said relatively thin and pliable wall is striated to allow easier passage of the member through said tube.

4. The transnasal conduit of claim 1, wherein said open proximal end is flared for easier introduction of the member into said tube.

5. The transnasal conduit of claim 1, wherein said clamping means further comprises:

a collar, said collar circumscribing said tube, said collar having a threaded aperture formed therethrough in a generally perpendicular orientation with respect to said thin and pliable wall; and a thumbscrew, said thumbscrew threadingly engaging said threaded aperture, said thumbscrew projecting against said thin and pliable wall when increasingly threaded into said threaded aperture to compresses said thin and pliable wall and thereby reduce said inner diameter of said tube.

6. A transnasal conduit for atraumatically guiding a sensor probe through delicate mucosal passages of a patient, comprising:

a tube, said tube having a relatively thin and pliable wall approximately one to three millimeters thick and a relatively wide inner diameter with respect to the mucosal passages approximately one centimeter in diameter, said relatively thin and pliable wall being striated to allow easier passage of a probe through said tube;

said tube having separate lobes formed on a distal end thereof, said separate lobes being contoured to be disposed in abutting relationship one to another for forming a normally closed distal end of said tube for promoting atraumatic travel of said tube through the mucosal passages, said separate lobes having interior protuberances formed thereon for elastically holding said lobes in said abutting relationship, said separate lobes being displaceable to open said distal end of said tube responsive to a force applied thereto by advancement of the probe through said tube;

said tube having a flared open proximal end for easier introduction of the probe into said tube and for providing an abutting surface that helps prevent migration of said tube further into a naris associated with the mucosal passages past said open proximal end;

pinch clamp means for pinching said thin and pliable wall of said tube to temporarily and releasably secure the probe within said tube, said pinch clamp means including (1) a collar circumscribing said tube, said collar having a threaded aperture formed therethrough and disposed in a generally perpendicular orientation with respect to said thin and pliable wall, and (2) a thumbscrew threadingly engaging said threaded aperture, said thumbscrew projecting against said thin and pliable wall when increasingly threaded into said threaded aperture;

a patient flange, said patient flange circumscribing said tube and having a pair of ears coupled thereto on opposing sides thereof; and an elastic strap for coupling said patient flange and said tube to the patient, said elastic strap having a pair of opposing ends respectively coupled to said pair of ears.

7. A method for transnasally and generally atraumatically intubating a patient with a transesophageal echocardiography sensor (TEE sensor), the steps comprising:

providing a transnasal conduit having separate lobes formed on a distal end thereof to define a closed end contour;

inserting a TEE sensor into said transnasal conduit and forming a sensor-conduit assembly;

nasally intubating the patient with said sensor-conduit assembly;

extending the TEE sensor through said transnasal conduit to displace said separate lobes and thereby open said distal end, said TEE sensor being advanced sufficiently to engage the patent's esophagus with the TEE sensor;

temporarily securing the TEE sensor to said transnasal conduit; and temporarily securing said transnasal conduit to the patient.

8. A transnasal conduit for atraumatically guiding a member through delicate mucosal passages of a patient, comprising:

a tube, said tube having a relatively thin and pliable wall and a relatively wide inner diameter with respect to the mucosal passages, said tube being striated to allow easier passage of a member through said tube;

said tube having an open proximal end for introduction of the member into said tube;

said tube having a plurality of separate lobes formed at a distal end of said tube, said plurality of lobes being contoured to be disposed in abutting relationship for forming a normally closed distal end for promoting atraumatic travel of said tube through the mucosal passages, said plurality of separate lobes being displaceable to open said distal end of said tube responsive to a force applied thereto by advancement of the member through said tube;

a flange, said flange circumscribing said open proximal end of said tube, said flange providing an abutting surface that helps prevent migration of said tube further into a naris associated with the mucosal passages past said open proximal end; and clamping means for depressing said thin and pliable wall of said tube to temporarily and releasably clamp the member to said tube.

9. A transnasal conduit for atraumatically introducing a patient monitoring sensor through delicate mucosal passages of a patient, comprising:

a member having a distal end with the sensor coupled thereto;

a tube, said tube having a relatively thin and pliable wall and a relatively wide inner diameter with respect to the mucosal passages, said tube having an open proximal end for introduction of said member into said tube, said tube having a plurality of separate lobes formed at a distal end of said tube, said plurality of lobes being disposed in abutting relationship to form said distal end of said tube in a normally closed condition for promoting atraumatic travel of said tube through the mucosal passages, said plurality of separate lobes being displaceable to open said distal end responsive to a force applied thereto by advancement of the member through said tube;

a flange, said flange circumscribing said open proximal end of said tube, said flange providing an abutting surface that helps prevent migration of said tube further into a naris associated with the mucosal passages past said open proximal end; and clamping means disposed adjacent said flange for depressing said thin and pliable wall of said tube to temporarily clamp said member to said tube for forming an assembly to be inserted into the mucosal passages, said clamping means being releasable to permit advancement of said member past said plurality of lobes to expose said distal end of said member for contact with the patient.

10. The transnasal conduit of claim 9, wherein said separate lobes comprise interior protuberances promoting closure of said normally closed distal end.

* * * * *